United States Patent
Scubla et al.

(10) Patent No.: US 7,947,855 B2
(45) Date of Patent: May 24, 2011

(54) PROCESS FOR THE PURIFICATION OF 1,4-BUTANEDIOL MONONITRATE

(75) Inventors: Tiziano Scubla, Pasian Di Prato (IT); Nevio Francescutti, San Giovanni Di Casarsa (IT); Fausto Gorassini, Udine (IT); Graziano Castaldi, Briona (IT)

(73) Assignee: Dipharma S.p.A., Mereto di Tomba (IT)

( * ) Notice: Subject to any disclaimer, the term of this patent is extended or adjusted under 35 U.S.C. 154(b) by 386 days.

(21) Appl. No.: 12/166,739

(22) Filed: Jul. 2, 2008

(65) Prior Publication Data

US 2008/0293961 A1    Nov. 27, 2008

Related U.S. Application Data

(62) Division of application No. 10/534,867, filed as application No. PCT/EP03/12375 on Nov. 6, 2003, now abandoned.

(30) Foreign Application Priority Data

Nov. 14, 2002   (IT) .............................. MI2002A2409

(51) Int. Cl.
*C07C 27/26*    (2006.01)
*C07C 201/02*   (2006.01)

(52) U.S. Cl. ........ 568/840; 568/852; 568/868; 558/483; 558/484

(58) Field of Classification Search .................. 568/840, 568/852, 868; 558/484
See application file for complete search history.

(56) References Cited

FOREIGN PATENT DOCUMENTS

| WO | WO 98/25918 | 6/1998 |
|----|-------------|--------|
| WO | WO 01/10814 | 2/2001 |

OTHER PUBLICATIONS

International Search Report dated Mar. 16, 2004, in PCT application.
K. Treves et al., "Henry's law constants of some beta-, gamma- and delta-hydroxy alkyl nitrates of atmospheric interest", Environ. Sci. Technol., vol. 34, 2000, pp. 1197-1203, XP002271697, experimental section; method 1 p. 1200, left-hand column, paragraph 1, table 1.
Kirk-Othmer, "Extraction (liquid-liquid)", Encyclopedia of Chemical Technology, vol. 10, 1993, pp. 136-139, XP002271719, the whole document.

*Primary Examiner* — Sikarl A Witherspoon
(74) *Attorney, Agent, or Firm* — Young & Thompson

(57) ABSTRACT

A process for the purification of 1,4-butanediol mononitrate from 1,4-butanediol dinitrate and 1,4-butanediol, by selective extraction with solvents is herein disclosed.

10 Claims, 1 Drawing Sheet

PROCESS FOR THE PURIFICATION OF 1,4-BUTANEDIOL MONONITRATE

CROSS-REFERENCE TO RELATED APPLICATION

Figure 1:
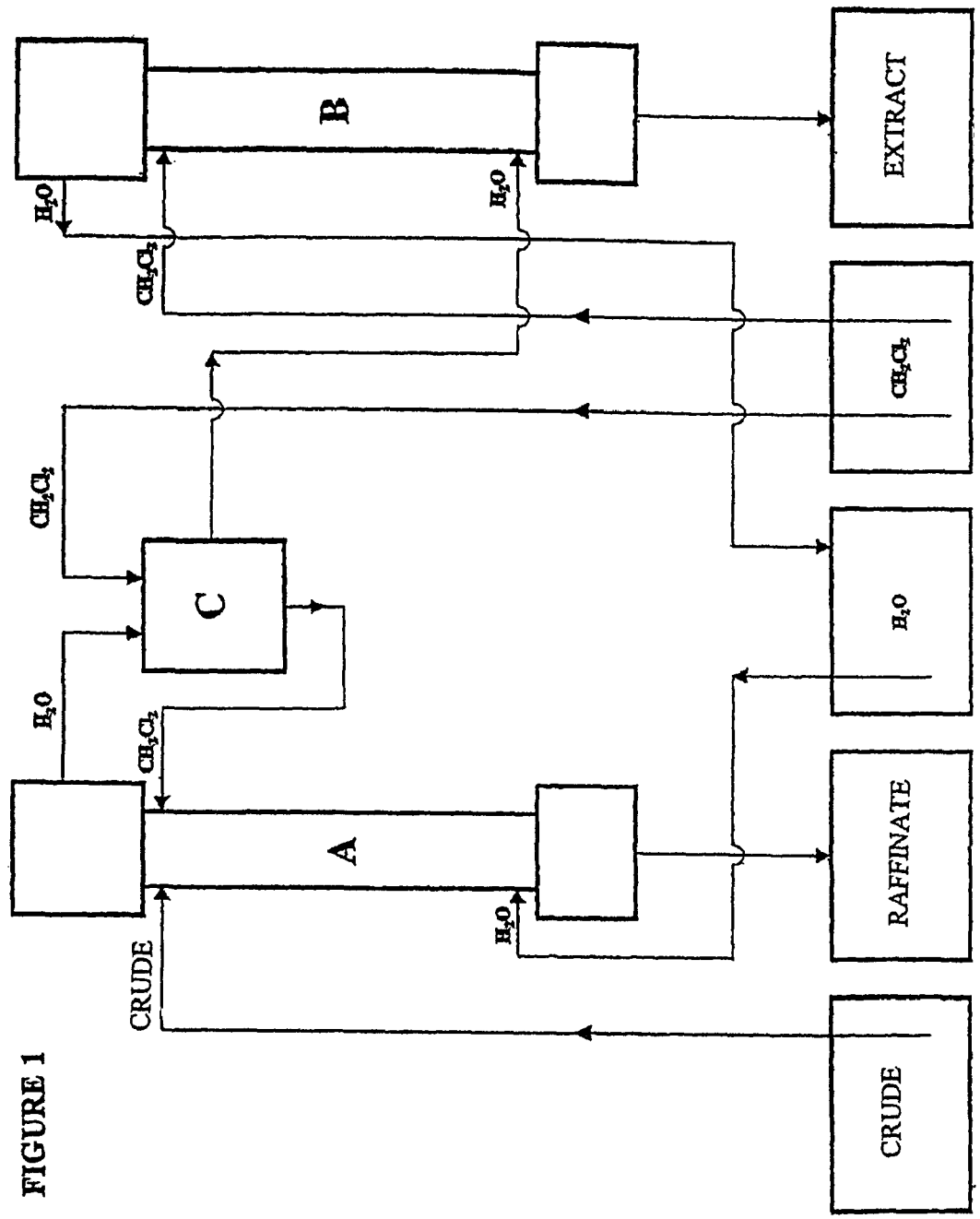

The present application claims the 35 U.S.C. §120 benefit of prior U.S. patent application Ser. No. 10/534,867 filed May 12, 2005, which is incorporated herein by reference, and to which the present application is a divisional US national non-provisional utility patent application.

FIELD OF THE INVENTION

The present invention relates to a process for the purification of 1,4-butanediol mononitrate (BDMN) from 1,4-butanediol dinitrate (BDDN) and 1,4-butanediol (BD) in an efficient, easily controllable way, which is therefore safer for operators.

TECHNOLOGICAL BACKGROUND

BDMN is a key intermediate in the synthesis of nitric oxide (NO)-releasing NSAIDs, i.e. non-steroidal anti-inflammatory drugs which release nitric oxide. NO-NSAIDs have antipyretic and anti-inflammatory activities, but lower gastrointestinal toxicity than other non-steroidal anti-inflammatory medicaments. Examples of NO-NSAIDs are NO-acetylsalicylic acid, NO-diclofenac, NO-naproxen, NO-ketoprofen and NO-ibuprofen. The preparation of NO-naproxen is described, for example, in WO 01/10814.

The industrial production of BDMN by reduction or hydrolysis from BDDN, is problematic and poorly selective, as the synthesis of BDDN involves problems concerning production, storage and transport similar to those connected with the use of nitroglycerin.

Mono-nitration of BD with the methods available to date is also problematic and poorly selective on an industrial scale, as dangerous decomposition reactions easily occur when a strong oxidizer (nitric acid) is contacted with an unstable substrate.

Moreover, BDMN obtained by mono-nitration of BD has to be separated from unreacted BDDN and BD. Such separation is, however, potentially dangerous, in that BDMN has, like BDDN, explosive characteristics, therefore neither crystallization nor distillation techniques can be employed. In fact, both BDMN and BDDN are liquid at room temperature and they can decompose upon crystallization due to friction or impaction. Analogously, distillation involves evident hazards owing to the recovery of the explosive compound in the pure form. In view of their chemical-physical characteristics, distillation of a mixture containing BDDN and BDMN would require heating to a temperature at which spontaneous, explosive decomposition could take place.

There is therefore need for a process for the purification of BDMN from BD and BDDN which avoids crystallization or distillation.

DETAILED DISCLOSURE OF THE INVENTION

It has now been found that BDMN can be selectively separated from BD and BDDN in industrially advantageous yields by subsequent extractions with water and a water-immiscible organic solvent.

Object of the present invention is therefore a process for the separation of 1,4-butanediol mononitrate from a solution of 1,4-butanediol dinitrate and 1,4-butanediol in a water-immiscible organic solvent, which process comprises the following steps:
a) extraction of BDMN from said solution by water;
b) extraction of BDMN from the resulting aqueous solution, by an organic solvent immiscible with water.

According to a preferred aspect, the invention comprises a further step c), which consists in washing the aqueous solution exiting from the extraction column "(A)" with the same organic solvent used in the subsequent step b). Said washing allows to remove BDDN from the aqueous phase before subjecting it to step b).

According to a further preferred aspect, the invention comprises a further step d) in which the residual organic solution from step a) is extracted with the aqueous phase exiting from column (B). The resulting BDMN-enriched aqueous solution is recycled to the first extraction column (A).

Typical water-immiscible organic solvents which can be used according to the invention are chlorinated solvents, for example C1-C4 alkyl mono-, di-, tri- or tetrachlorides, preferably dichloromethane, trichloromethane, tetrachloromethane, trichloroethane and tetrachloroethane, in particular dichloromethane. Preferably, the water-immiscible organic solvent in the solution of BD, BDMN and BDDN to be subjected to the separation process and the water-immiscible organic solvent used in the extraction according to step b) are the same.

The process according to the invention consists of one or more extraction cycles with water and a water-immiscible organic solvent according to steps a) and b) and optionally of steps c) and/or d). Preferably, the process comprises 1 to 4 a) and b) cycles, preferably 2 or 3, most preferably 2.

If desired, the organic solution containing purified BDMN obtained with the process of the invention can be concentrated.

A further object of the invention is highly pure 1,4-butanediol mononitrate, typically higher than 99% pure, as obtainable by the process of the invention.

A further object of the invention is a solution of 1,4-butanediol mononitrate in a water-immiscible organic solvent, substantially free from 1,4-butanediol dinitrate, as obtainable by the process of the invention.

Solutions of 1,4-butanediol mononitrate substantially free from 1,4-butanediol dinitrate in an organic solvent selected from dichloromethane, trichloromethane, tetrachloromethane, tricloethane and tetrachloroethane, in particular dichloromethane, are preferred.

The solution containing BDMN, BDDN and BD to be subjected to the extraction process according to the invention can be obtained either with conventional synthetic methods in a water-immiscible solvent or with a novel process for the mononitration of 1,4-butanediol, which is a further object of the invention.

Said method consists in the nitration of 1,4-butanediol by treatment with "stabilized" nitric acid in a water-immiscible organic solvent selected from those defined above.

The expression "stabilized" nitric acid means a nitric acid solution diluted with water, having concentration ranging from about 83 to about 85%, preferably from about 84.5 to about 84.8%, and substantially free from nitrous acid and nitrogen oxides. The expression "substantially free from nitrous acid and nitrogen oxides" means that their concentration is typically lower than 10 ppm, preferably lower than 5 ppm. Said "stabilized" nitric acid is also an object of the present invention.

The preparation of "stabilized" nitric acid can be carried out, for example, by dilution of fuming nitric acid with water to a concentration ranging from about 83 to about 85% followed by treatment with an amount of an agent able to remove nitrous acid and nitrogen oxides present therein. Said agent can be, for example, urea or sulfamic acid, preferably urea, in amounts ranging from about 0.3 to about 1% w/w. The same result can be obtained by addition of an aqueous solution of said agent to fuming nitric acid. The contact time of said agent with nitric acid required to completely remove the nitrous acid and nitrogen oxides ranges from about 80 minutes to about 130 minutes. When said agent is urea, the amount ranges from about 0.6 to about 1% w/w, preferably from about 0.7 to about 1% w/w and the contact time preferably ranges from about 95 to about 120 minutes.

The "stabilized" nitric acid according to the invention should be used within approx. three hours from stabilization, as in time nitrous acid and nitrogen oxides are released again in such concentrations as to trigger strong decomposition reactions.

The weight ratio of "stabilized" nitric acid to 1,4-butanediol preferably ranges from about 11:1 to about 14.5:1 and the nitration is preferably carried out for a time ranging between about 10 and about 30 minutes.

In this manner industrially advantageous yields in 1,4-butanediol mononitrate are obtained and hazards for operators are lower than those associated with nitration with concentrated nitric acid, sometimes added with sulfuric acid or urea to remove nitrous acid.

Before being subjected to the extraction process of the invention, the nitrated solution can be treated to remove by-products and unreacted starting products, then suitably concentrated. Said solution is, in fact, a crude mixture of BDMN, by-product BDDN, unreacted BD and nitric acid in the organic solvent, also containing other by-products deriving from dehydration and/or oxidation. The solution is first partially neutralized with a sodium hydroxide concentrated solution, thus extracting most of the unreacted BD in the resulting sodium nitrate aqueous solution. The organic phase is then concentrated by evaporation and neutralized with a diluted basic solution.

The solution subjected to the separation process of the invention preferably contains BDMN in amounts ranging from about 11% to about 15% w/w, preferably 11% w/w; BDDN in amounts ranging from about 3 to about 4.5% w/w, preferably 4%; BD in amounts ranging from about 0.2 to about 0.8% w/w (with respect to BDMN). The extraction is more efficient with more concentrated solutions, but when total nitroesters concentrations are above 15% w/w, the solutions have explosive character.

The extraction according to steps a) and b) is preferably carried out using two or more liquid-liquid counter-current extraction columns, preferably two, three or four, more preferably two, herein referred to as column (A), for step a) and column (B), for step b). Columns (A) and (B) are preferably plate columns having 45-55 plates and optionally a decanter at the top and one at the bottom. Particularly suitable are liquid-liquid counter-current extraction columns for nominal flow rates of about 5-50 l/h, with a decanter at the top and one at the bottom. According to a particularly preferred extraction method, said extractions are carried out with columns mod. E60/50G from Kühni (Basilea-Switzerland).

The two extractions are carried out at temperatures compatible with the thermal stability of BDMN and BDDN, namely at a temperature below the boiling point of the organic solvent, preferably at room temperature.

FIG. 1 shows the essential elements of a purification plant according to the invention, namely extraction column (A), extraction column (B) and a reactor (C) for the optional step c), wherein the process is carried out using dichloromethane as the solvent. When dichloromethane is replaced with an organic solvent lighter than water, fluids will be fed to the extraction columns (A) and (B) in an opposite manner.

For extraction step a), the dichloromethane solution of BDMN, BDDN and BD, i.e. the "crude" obtainable form the treatment described above, is fed to the top of a first extraction column (A), while water is fed to the bottom of said column. All the residual BD, most of the BDMN and a very small aliquot of BDDN in aqueous solution exit the top decanter of column (A). The raffinate consisting of a dichloromethane solution containing most of the BDDN and a small amount of BDMN exits the bottom of the column.

For extraction step b), the aqueous solution of BDMN, residual BD and the very small amount of BDDN from the first extraction column (A) is fed to the base of a second extraction column (B), while fresh dichloromethane is fed to the head. Water with all the residual BD and some BDMN exit the head of the second column, while the extract, i.e. a dichoromethane solution containing purified BDMN and the negligible amount of BDDN, exit the bottom.

Optional step c), which is carried out in an extractor (C), allows to increase the purity level of BDMN and can be effected as follows. The aqueous solution exiting the first extraction column (A) is treated with a suitable amount of dichloromethane ranging from about 7 to about 20% w/w with respect to the chloromethylene solution fed to the column (A). Treatment allows to remove BDDN which, although sparingly water-soluble (solubility <0.05%), is still present at rather high concentrations compared with BDMN (approx. 1-2%). Extractor (C) can be, for example, a conventional reactor, with a decanter downstream. After decantation, the aqueous phase now substantially containing only BDMN and the residual BD is fed to the second extraction column (B). The organic phase containing BDDN is recycled.

For step d), the aqueous phase from the second extraction column (B), containing a very small amount of BDMN, is mixed with the dichloromethane raffinate from column (A), which in turn contains a small amount of BDMN. Extraction and subsequent decantation provide an aqueous phase enriched in BDMN, which is recycled to the first extraction column (A). In this manner, yield in BDMN can be further increased.

From the scheme reported in FIG. 1 it is evident that the process of the invention also provides a remarkable savings of extraction water. In fact, water that contains the residual BD exiting the top of the second extraction column (B) is recycled to the first extraction column (A) until its content in BD is compatible with the extraction process.

From the above description it will be appreciated that the process of the invention allows to separate BDMN from BD and BDDN with low hazards, good selectivity and high yields. The extraction yield (expressed as percentage ratio of purified BDMN to BDMN present in the crude solution) is above 90% w/w.

Furthermore, the resulting organic solution contains highly pure BDMN, typically above 99.0% pure. For example, the dichloromethane solution contains BDMN with purity from about 99.5 to about 99.9%, in amounts ranging from about 5 to about 8% w/w. The solution is therefore substantially free from BDDN. The residual amount of BDDN in the organic solvent is, in fact, below 0.2% and in case of dichloromethane is below 0.15%.

If desired, once the extraction is completed, the purified BDMN organic solution can be finally concentrated, for example under reduced pressure, to a concentration of about 15% w/w in order to make transport or storage easier. The use of solutions with higher BDMN contents can be potentially dangerous to operators.

The present invention is further illustrated by the following examples.

EXAMPLES

Example 1

Purification with Water/Dichloromethane

Two extraction columns Kühni mod. E60/50G are used. The crude solution (containing about 11% BDMN and about 4% BDDN) is fed (6.5 kg/h) to the top of the first column, wherein it encounters the extracted water (42.3 kg/h) (containing about 0.3% of BDMN) that exit the top of the second column and flows backwards. The raffinate (containing about 0.6% BDMN and about 6% BDDN) exits the bottom of the first column and extraction water (42.9 kg/h), rich in BDMN (about 1.6% BDMN and <0.05% BDDN) exits the top and is passed through de-emulsifier, then fed to the bottom of the second column, wherein it encounters fresh dichloromethane flowing backwards (11.1/h). Water with some BDMN exits the top of second column and is recycled to the first column, while the dichloromethane solution containing purified BDMN (about 6% w/w BDMN) exits the bottom. BDMN, which has 99.5% purity (0.5% of BDDN) in the extract, is then concentrated to 15% w/w. The extraction yield, expressed as the ratio of purified BDMN to BDMN present in the crude solution, is about 94% w/w.

Example 2

Purification with Water/Dichloromethane

The plant is substantially the same as that of example 1, in which a 5 liters reactor equipped with a stirring system and a separator is fitted between the two distillation columns. In this step, BDDN solubilised in the water exiting the top of the first column is extracted with dichloromethane (1.0 kg/h) and recycled after separation. The final extract is thus sufficiently pure (BDDN <0.1%).

Example 3

Preparation of "Stabilized" Nitric Acid

A stainless steel reactor, equipped with condenser and stirrer, is loaded with 90 kg of diluted nitric acid (84.7%), with nitrous acid content of approx. 0.09%. The nitric acid solution is added with 675 g of urea beads, under stirring. The solution is kept under stirring for about 90 minutes, then disappearance of all the nitrous acid and nitrogen oxides is checked, both by observation of the color of the solution and determination with permanganate. If necessary, further urea is added in small portions, until complete removal of the nitrous acid and nitrogen oxides.

Example 4

1,4-Butanediol-mononitrate

A stainless steel reactor is loaded in succession with 931 g of dichloromethane and 385 g of "stabilized" nitric acid. The dispersion is cooled to about 0° C. under stirring, then 50 g of a 70/30 solution of 1,4-butanediol in dichloromethane is added in a single portion. The reaction mixture is kept under stirring at temperatures ranging from about −2° C. to 2° C. Nitration kinetics is monitored on samples of the reaction mixture. After 20 minutes the reaction is quickly quenched by pouring it into an ice/water (385 g) mixture, then neutralized with 433 g of 40% NaOH, keeping the temperature below 15° C. The organic phase containing 1,4-butanediol-mononitrate (19.2 g), 1,4-butanediol-dinitrate (6.4 g) and 1,4-butanediol (0.1 g) is then separated and subjected to the subsequent purification.

The invention claimed is:

1. A process for the selective purification of 1,4-butanediol mononitrate from a solution of 1,4-butanediol dinitrate and 1,4-butanediol in a water-immiscible organic solvent, comprising the steps of:
   a) extracting 1,4-butanediol mononitrate from said solution by water under conditions selected to separate 1,4-butanediol and 1,4-butanediol mononitrate from 1,4-butanediol dinitrate; and
   b) extracting 1,4-butanediol mononitrate from the resulting aqueous solution to obtain purified 1,4-butanediol mononitrate, by a water-immiscible organic solvent under conditions selected to separate 1,4-butanediol mononitrate from 1,4-butanediol.

2. The process as claimed in claim 1, wherein the extracting steps a) and b) are carried out in counter-current in two or more extraction columns.

3. The process as claimed in claim 1, wherein the extracting steps a) and b) are carried out in counter-current in 2, 3 or 4 extraction columns.

4. The process as claimed in claim 3, wherein the extracting steps a) and b) are carried out in counter-current in 2 extraction columns.

5. The process according to claim 1 further comprising washing the aqueous phase from step a) with the same water-immiscible organic solvent as that used in the subsequent step b).

6. The process according to claim 1, comprising extracting the resulting organic solution from step a) with the aqueous phase from step b) and the recycle of the aqueous solution to the extraction column of step a).

7. The process according to claim 1, comprising 1 to 4 cycles of extracting according to steps a) and b).

8. The process according to claim 1, wherein the water-immiscible organic solvent is an organic chlorinated solvent.

9. The process as claimed in claim 8, wherein the chlorinated solvent is selected from the group consisting of dichloromethane, trichloromethane, tetrachloromethane, trichloroethane and tetrachloroethane.

10. The process as claimed in claim 9, wherein the chlorinated solvent is dichloromethane.

* * * * *